(12) United States Patent
Lin et al.

(10) Patent No.: US 7,227,534 B2
(45) Date of Patent: Jun. 5, 2007

(54) OZONE DISINFECTING MOUSE

(76) Inventors: Yu-Yueh Lin, 3F, No. 17, Jiang Nan St., Neihu Chiu, Taipei (TW); Kun-Jung Yang, No. 40, Lane 113, Hangjou Rd., Jungli City, Taoyuan (TW)

( * ) Notice: Subject to any disclaimer, the term of this patent is extended or adjusted under 35 U.S.C. 154(b) by 436 days.

(21) Appl. No.: 10/806,463

(22) Filed: Mar. 23, 2004

(65) Prior Publication Data

US 2005/0212769 A1    Sep. 29, 2005

(51) Int. Cl.
*G09G 5/08* (2006.01)
(52) U.S. Cl. .................. 345/163; 345/156
(58) Field of Classification Search ........ 345/156–184; 422/186.07
See application file for complete search history.

(56) References Cited

U.S. PATENT DOCUMENTS 6,458,331 B1 * 10/2002 Roberts ............... 422/186.3
6,720,950 B2 * 4/2004 Cheng ..................... 345/163

FOREIGN PATENT DOCUMENTS

KR    2002023342 A   *  3/2002

* cited by examiner

*Primary Examiner*—Jimmy H. Nguyen
(74) *Attorney, Agent, or Firm*—Lowe Hauptman & Berner, LLP (57) ABSTRACT

A kind of ozone disinfecting non-cordless mouse that is installed with an internal ozone generator module, which is connected to the power of the USB (Universal Serial Bus) plug, such that the ozone generator can produce ozone gas during use of the mouse. The gas is dispelled through a suitable port in the carapace of the mouse, and can disinfect the mouse or its surrounding area, and disinfect or clean the surrounding air. The creation also includes an ozone disinfecting cordless mouse, in which an ozone generator module is installed in the interior of the receiver or recharger outlet of the mouse. This ozone generator module is powered by the existing power supply of the receiver or recharger outlet, and can produce ozone gas when the cordless mouse is inserted into the cradle of the receiver or recharger outlet. The resulting ozone gas is then dispelled through a suitable vent, and can disinfect the mouse or its surrounding area, and disinfect or clean the surrounding area.

8 Claims, 12 Drawing Sheets

OZONE DISINFECTING MOUSE

THE BACKGROUND OF THE INVENTION

This invention relates a mouse (computer mouse), and is more particularly to having ozone disinfection capabilities for purifying the air. This refers to mouses that have been outfitted with an ozone generator module (in the inside of non-cordless mouses or the inside of receiver or recharger outlet housing in cordless mouses) that produces and dispels ozone gas that can disinfect the mouse itself and its surroundings, as well as purify the air. This process occurs using the power from the USB (Universal Serial Bus) connector in non-cordless mouses or the outer power from receivers or power outlets in cordless mouses.

Generally, a mouse is an essential computer device that is used to input coordinates, select items, move items on the screen, etc. There are two general types of mouses, including cordless and non-cordless. Cordless mouses are typically connected to computers through a USB (Universal Serial Bus) plug to help conduct mouse operations using the computer's power. Cordless mouses are also generally connected to a computer through a USB (Universal Serial Bus) through a receiver or electrical outlet, such that the mouse operations are sent remotely through a cordless module in a receiver or electrical recharge outlet. Ordinary cordless mouses can also be rechargeable, with the help of a recharger cradle. During use, mouses are in constant contact with the human hand, yet most people do not wash their hands before using mouses, and commonly come in contact with other objects during mouse use, especially in locations such as banks, governmental institutions, or computer outlets, in which there are computers and mouses provided to the public for information needs. From this, we can see that the mouse is a breeding ground for germs, and can spread them though close contact with human hands. This invention was designed precisely for disinfection of mouses during use.

SUMMARY OF THE INVENTION

In one respect, the present invention is directly to provide ozone disinfecting cordless mouses that have been outfitted with an internal ozone generator module that produce and dispel ozone gas, thereby disinfecting the mouse itself and its surroundings, as well as purifying the air. These mouses are powered from the USB (Universal Serial Bus) connector in non-cordless mouses or the outer power from receivers or power outlets in cordless mouses.

In one embodiment of the present invention is to provide ozone disinfecting cordless mouses, specially equipped with ozone generator modules in the receiver or recharging outlet. These mouses are powered by the existing power supply in the receiver or recharging outlet, and produce ozone through the ozone generator module when placed in the docking bay of the receiver or recharger outlet. This ozone is then dispelled through a specialized vent onto the mouse, thus disinfecting the mouse or the area around it and/or cleaning or disinfecting the air.

BRIEF DESCRIPTION OF THE DRAWINGS

The foregoing aspects and many of the attendant advantages of this invention will becom more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
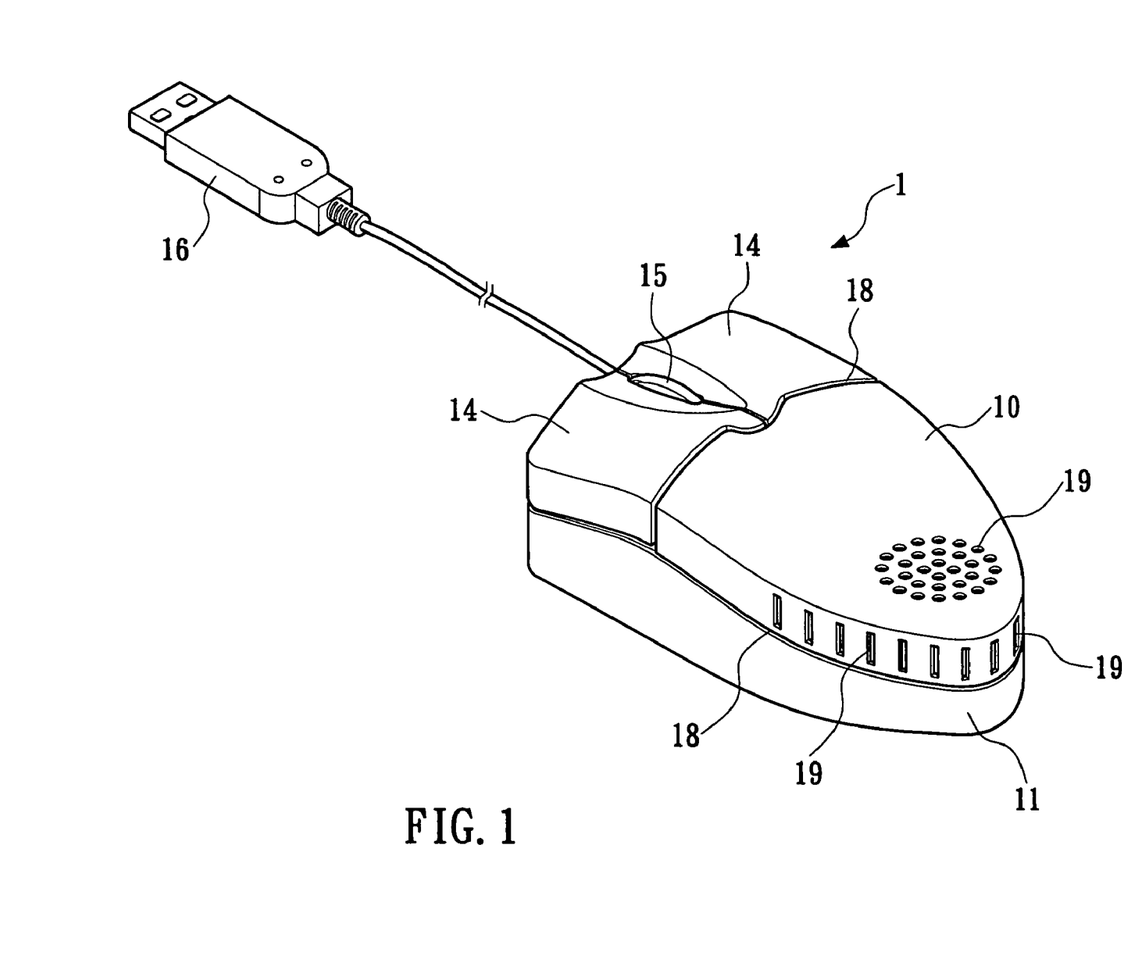
FIG. 1 is a 3D view of a non-cordless material of this present invention.
Figure 2:
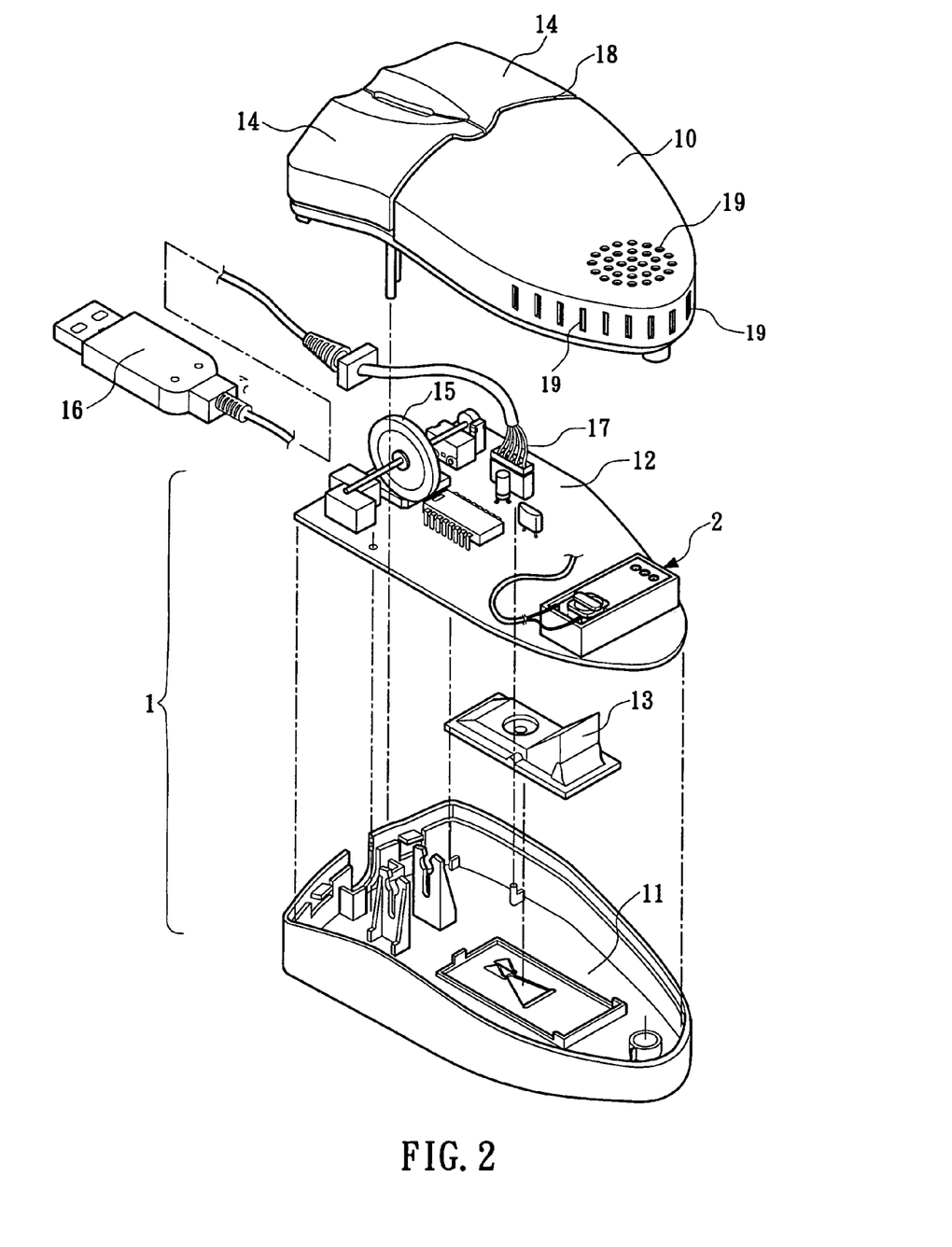
FIG. 2 is a exploded persepective view of FIG. 1.
Figure 3:
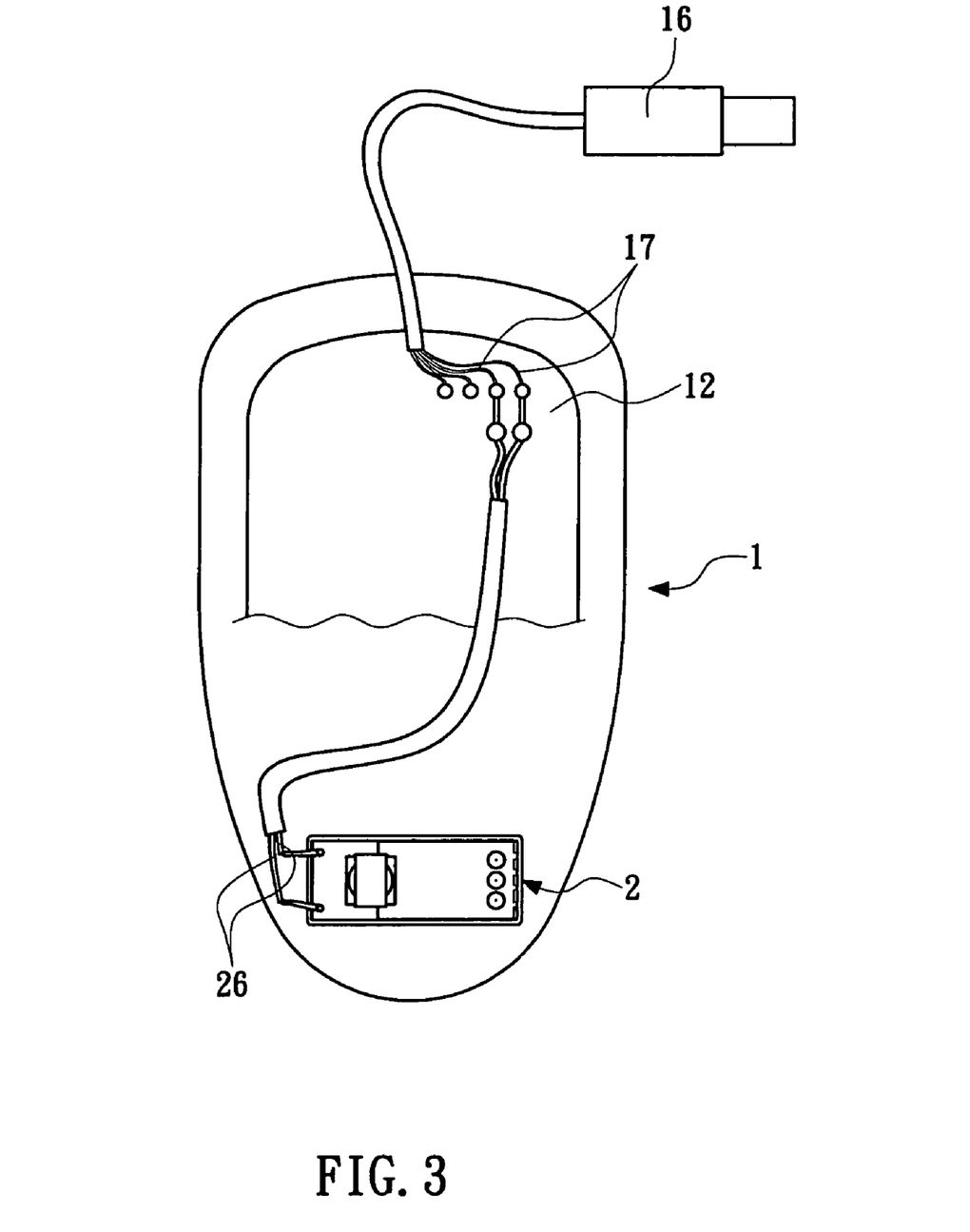
FIG. 3 is a Simplified circuit connectivity diagram of FIG. 1.
Figure 4:
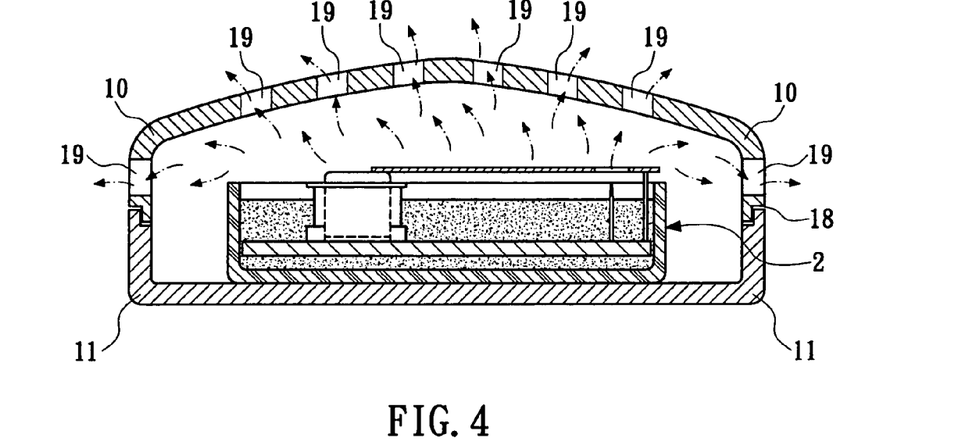
FIG. 4 is a rear elevational view of FIG. 1.
Figure 5:
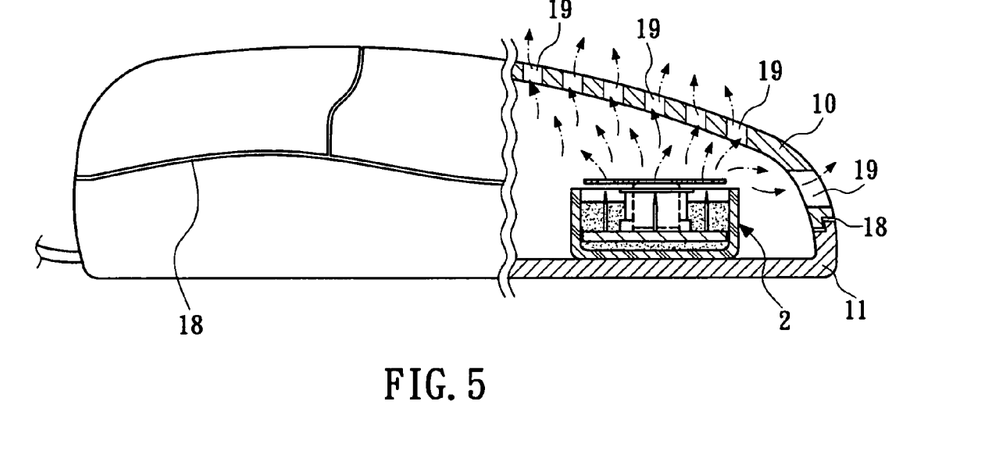
FIG. 5 is a sideview of FIG. 1.

The non-cordless mouse 1 as shown in FIGS. 1, 2, and 3 is a non-cordless mouse that includes a top carapace 10 and bottom carapace 11. Inside the carapace, there is a Micro Controller circuit board 12, an optical coordinates device 13 for coordinate signal output, and tow buttons 14 or reel wheel 15 for control signal output. In addition, the mouse can transmit signals to and receive power from the computer through a USB (Universal Serial Bus) connection plug 16. The special feature of this mouse is that a small ozone generator module 2 is installed in an appropriate location (for example, the aft portion of the non-cordless mouse) inside the carapace of the non-cordless mouse, such that the ozone generator module 2 is directly connected to the power cord 17 from the USB plug 16, and the ozone generator module 2 can utilize the existing power supply of the non-cordless mouse, as shown in FIG. 3. As a result, the non-cordless mouse can then generate ozone gas, and dispel it from a suitable vent in the carapace (for example, the boundary crevice 18 in the carapace of the mouse, or an additionally designed vent 19 in its upper carapace), as shown in FIGS. 4 and 5. Thus, the mouse is able prevent the accumulation or spreading of germs by disinfecting the mouse itself or the area around it (including the face of the hand that is directly in contact with the mouse), and/or clean or disinfect the surrounding air.

Figure 6:
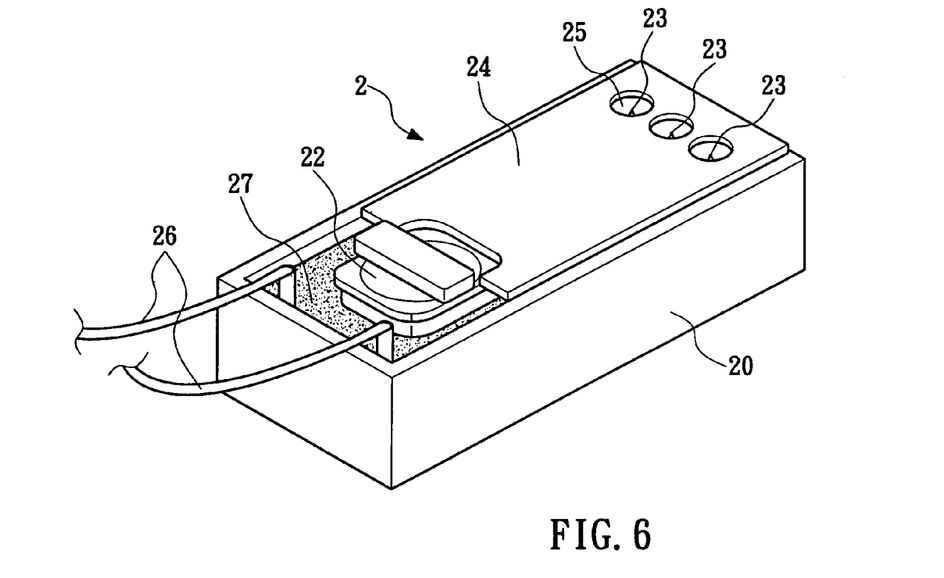
FIG. 6 is an enlargement view of of the ozone generator module of FIG. 1.
Figure 7:
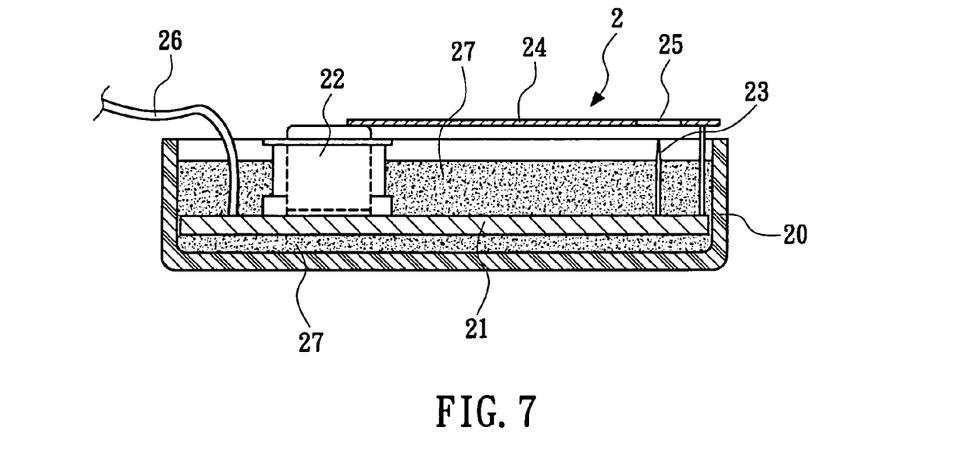
FIG. 7 is a side view of FIG. 6.
Figure 8:
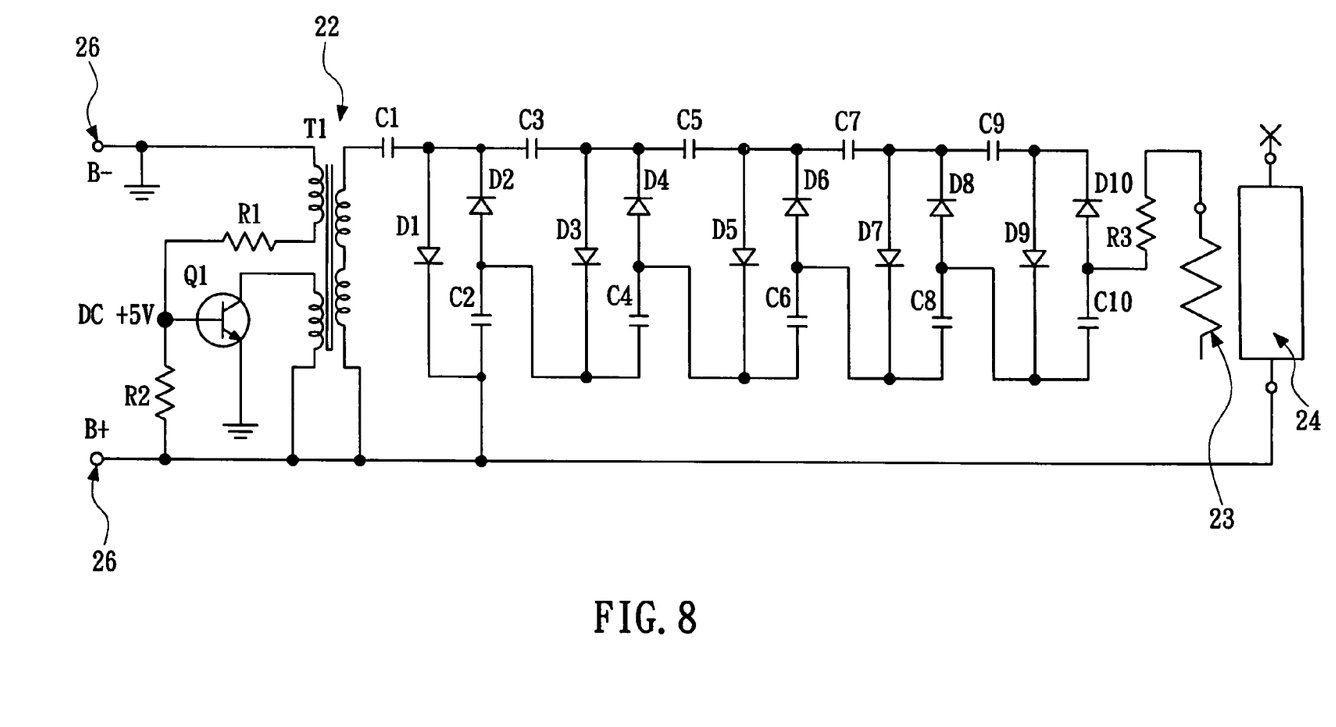
FIG. 8 is a circuit diagram of FIG. 6.
Figure 9:
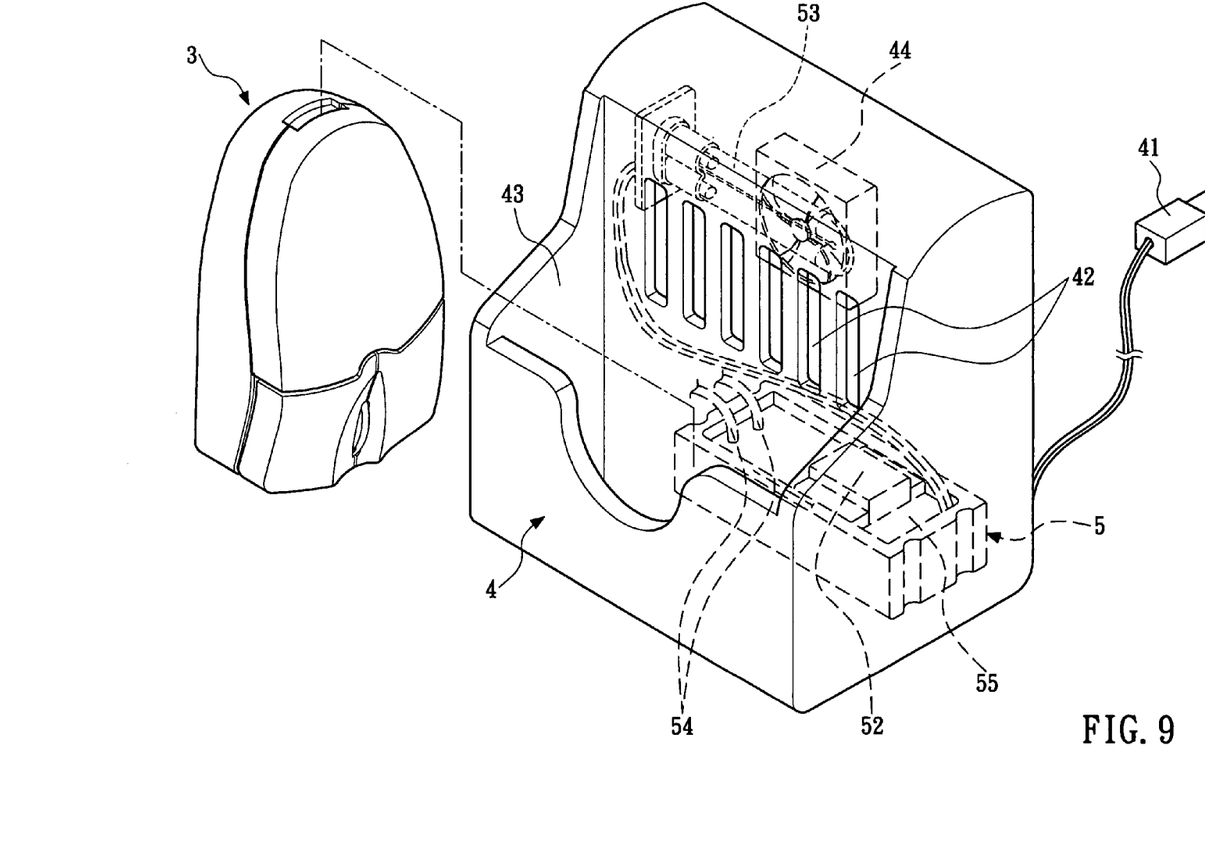
FIG. 9 is a 3D view of a cordless material of this present invention.
Figure 10:
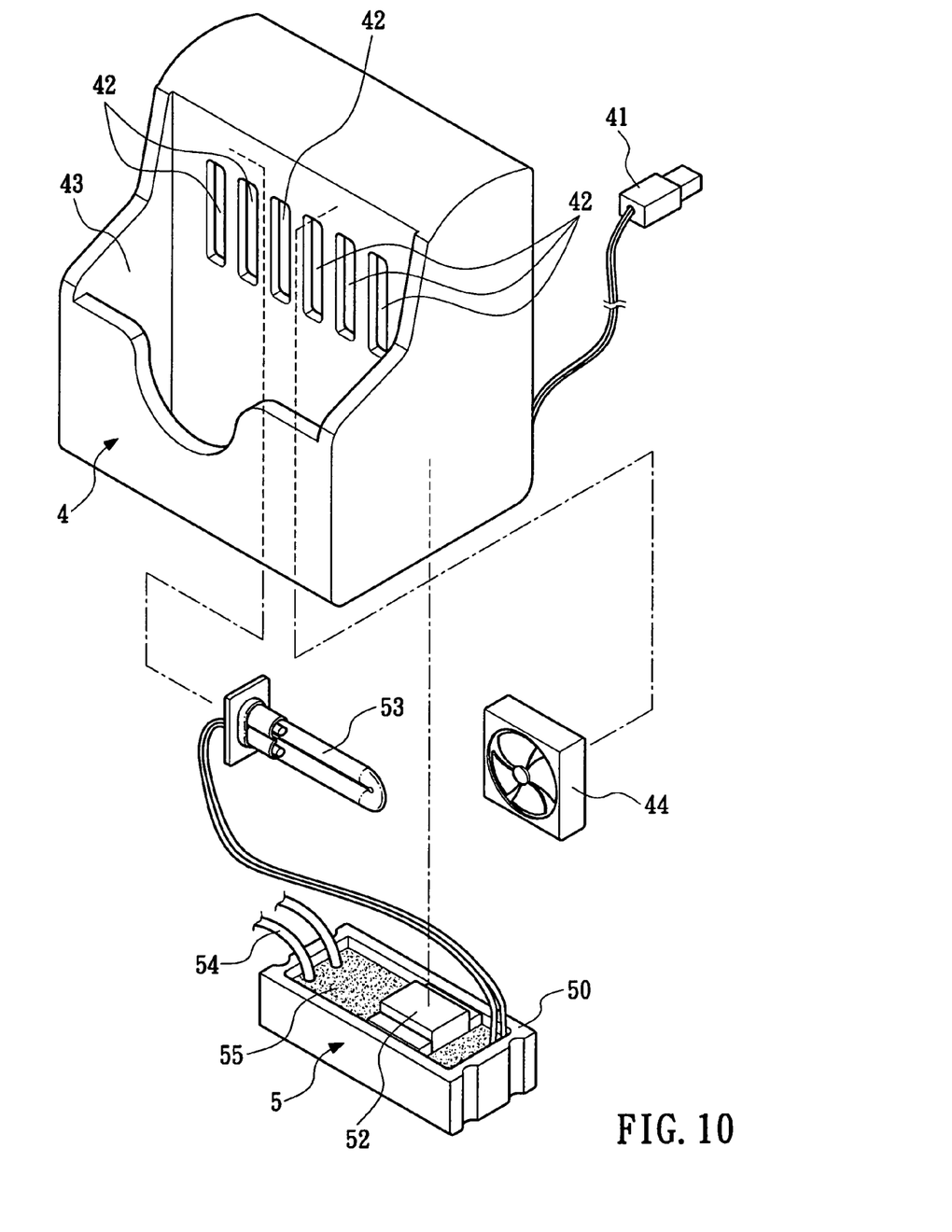
FIG. 10 is an exploded persepective view of the receiver (or recharger outlet) of FIG. 9.
Figure 11:
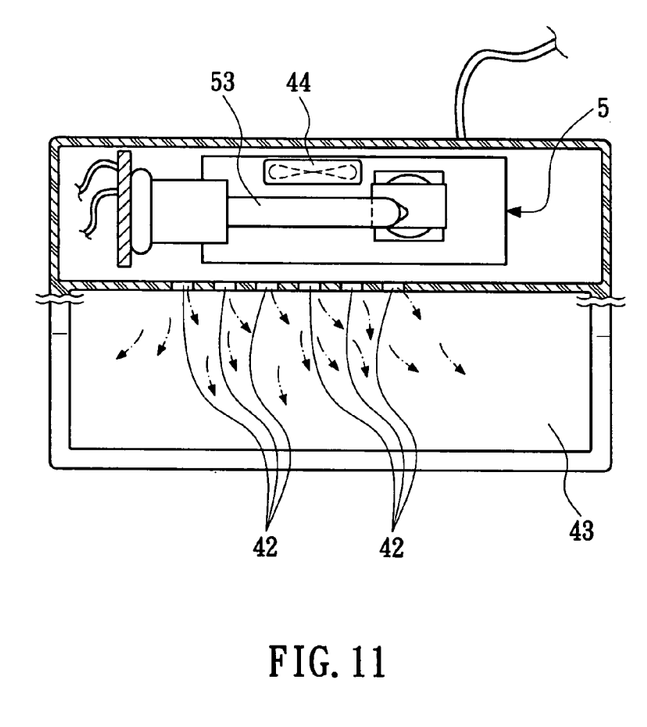
FIG. 11 is a front elevational view of FIG. 10.
Figure 12:
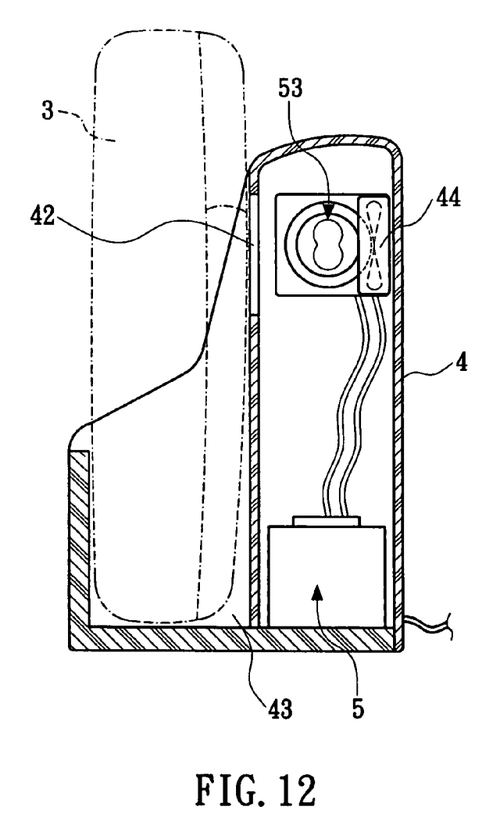
FIG. 12 is a side view of FIG. 9.
Figure 13:
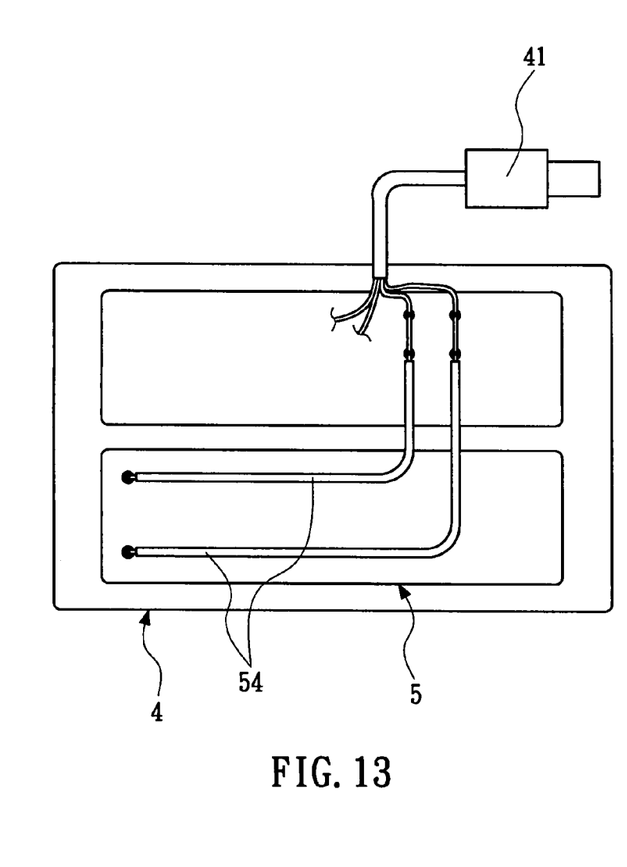
FIG. 13 is a diagram of circuit connectivity of FIG. 9.

As shown in FIGS. 6, 7, and 8, because mouses are only roughly the size of the human hand, there are inherent internal space limitations. In addition, mouses only utilize approximately 5 volts of power. This means that the ozone generator should be able to be easily installed in the mouse carapace, not affect its operation, and at the same time produce sufficient ozone gas using the existing power supply of the mouse. Thus, the ozone generator module used must at least meet the size and modulation requirements. Although the process by which the ozone generator module generates ozone gas utilizes the well-known point discharge principle, its structural design meets the requirements for the change in size and modulation. This includes an insulator box 20 (the square box shown in FIG. 6). At the bottom of the box, there is a circuit board 21, attached with a small transformer 22, as to allow the low voltage mouse to change to high voltage, low electric flow. Several electrode pins 23 are then attached onto the circuit board 21, as well as an electrode board 24 with opposing electrode pins 23. The electrode board 24 has separate holes 25 for each electrode pin 23, such that the center of each hole 25 is perfectly aligned with the point of each electrode pin 23. In addition, two wires (1 positive and 1 negative) should be connected from the circuit board to the power cord 17 from the USB plug 16. In addition, a layer of insulating resin 27 (such as Epoxy) is attached to the interior of the insulated box 20, such that it is sufficiently insulated. The above structure can effectively reduce the volume of the ozone generator module, thus allowing it to be easily installed and used in the body of the non-cordless mouse 1. During use, point discharge occurs from the electrode pins 23 after being contacted by the high voltage, and there is a surge in the electrodes in the holes 24 of the electrode board 24. This causes an ionization in the surrounding air, allowing the electric molecules to take on an extra anion, and become ozone. Negatively charged ions can also be produced from the point discharge of the circuit board shown in FIG. 8, thus creating the negative ion effect, that is beneficial to the human body.

As shown in FIGS. 9, 10, 11, 12, and 13. Cordless mouses 3 are remotely controlled devices used in tandem with receivers that are connected to a computer, and are not themselves directly connected to the power supply of computers. Cordless mouses 3 are generally used with an internal battery, and would be inconvenient due to short battery life if installed with an ozone generator model. Therefore, this project goes a step further with cordless mouses 3 by developing a receiver 4 or charger outlet (not shown in diagram) that is installed with an ozone generating module 5 that utilizes the existing power supply of the receiver 4 (in the case of a recharger outlet, the module would utilize the power supplied by an ordinary electric outlet (not shown). This ozone generator module 5 is able to produce ozone gas during use of the receiver, which is dispelled through a vent 43 in the receiver cradle, and can disinfect the body of the cordless mouse or its surroundings, and/or disinfect or clean the surrounding air.

Figure 14:
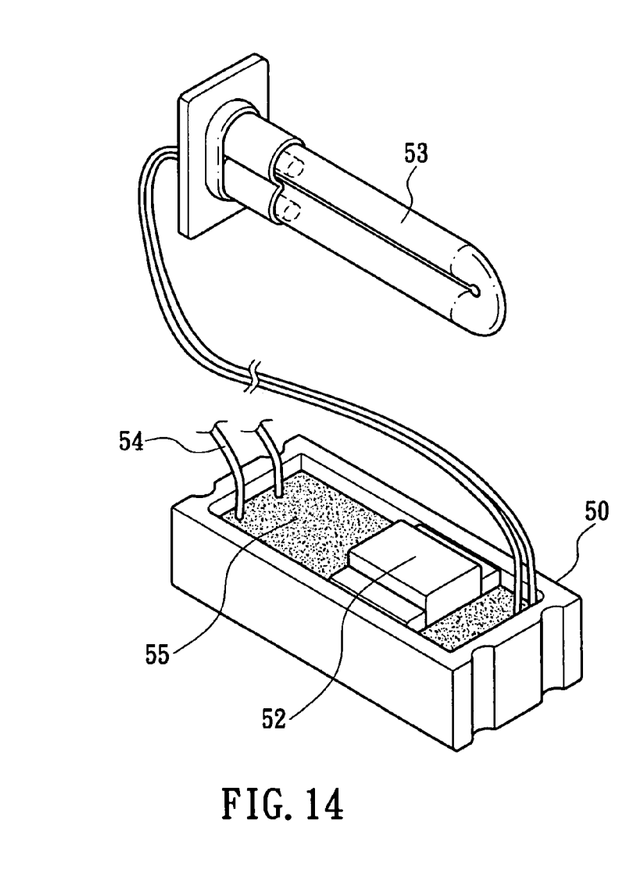
FIG. 14 is an enlargement view of the ozone generator module of FIG. 9.
Figure 15:
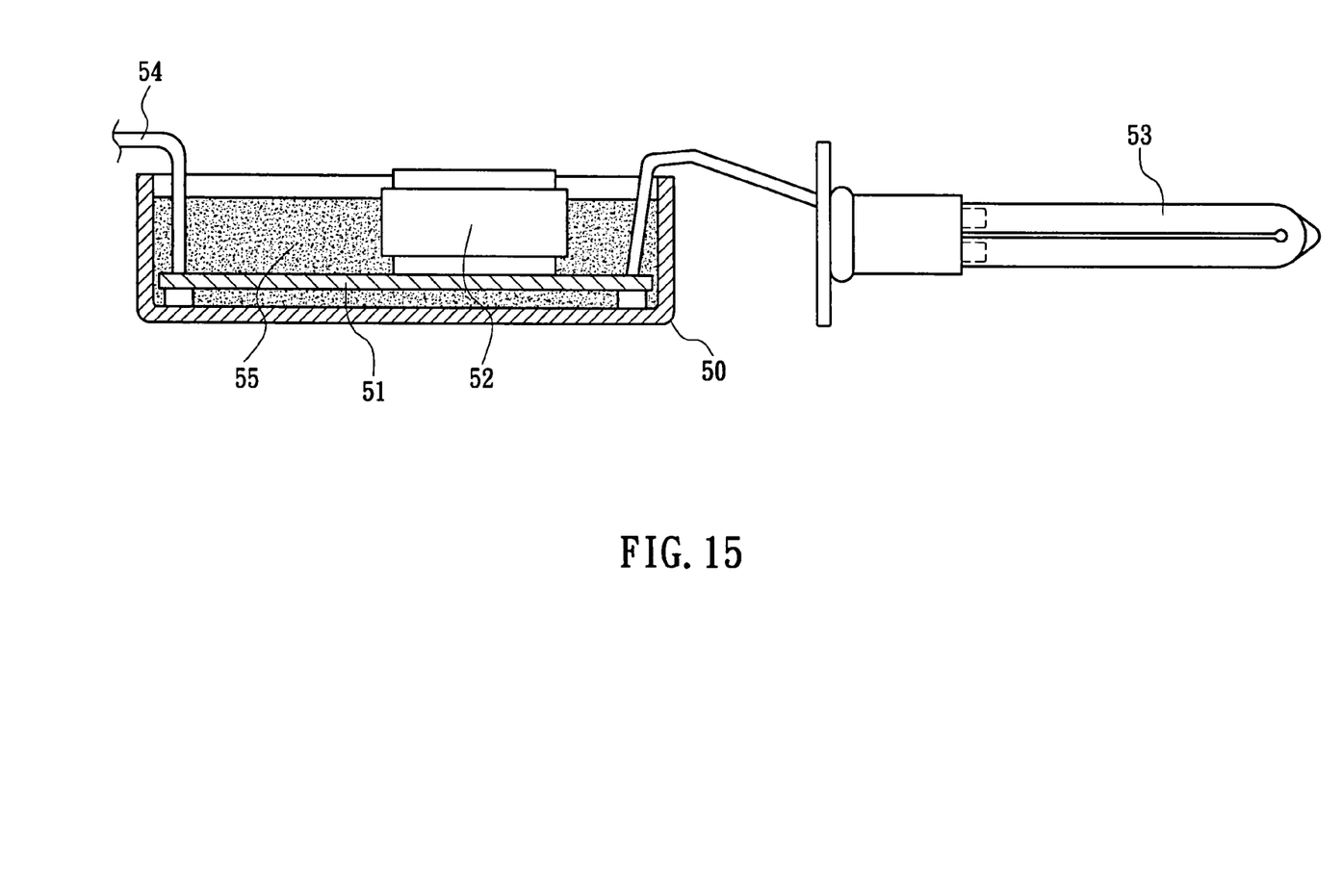
FIG. 15 is a sideview of FIG. 14.
Figure 16:
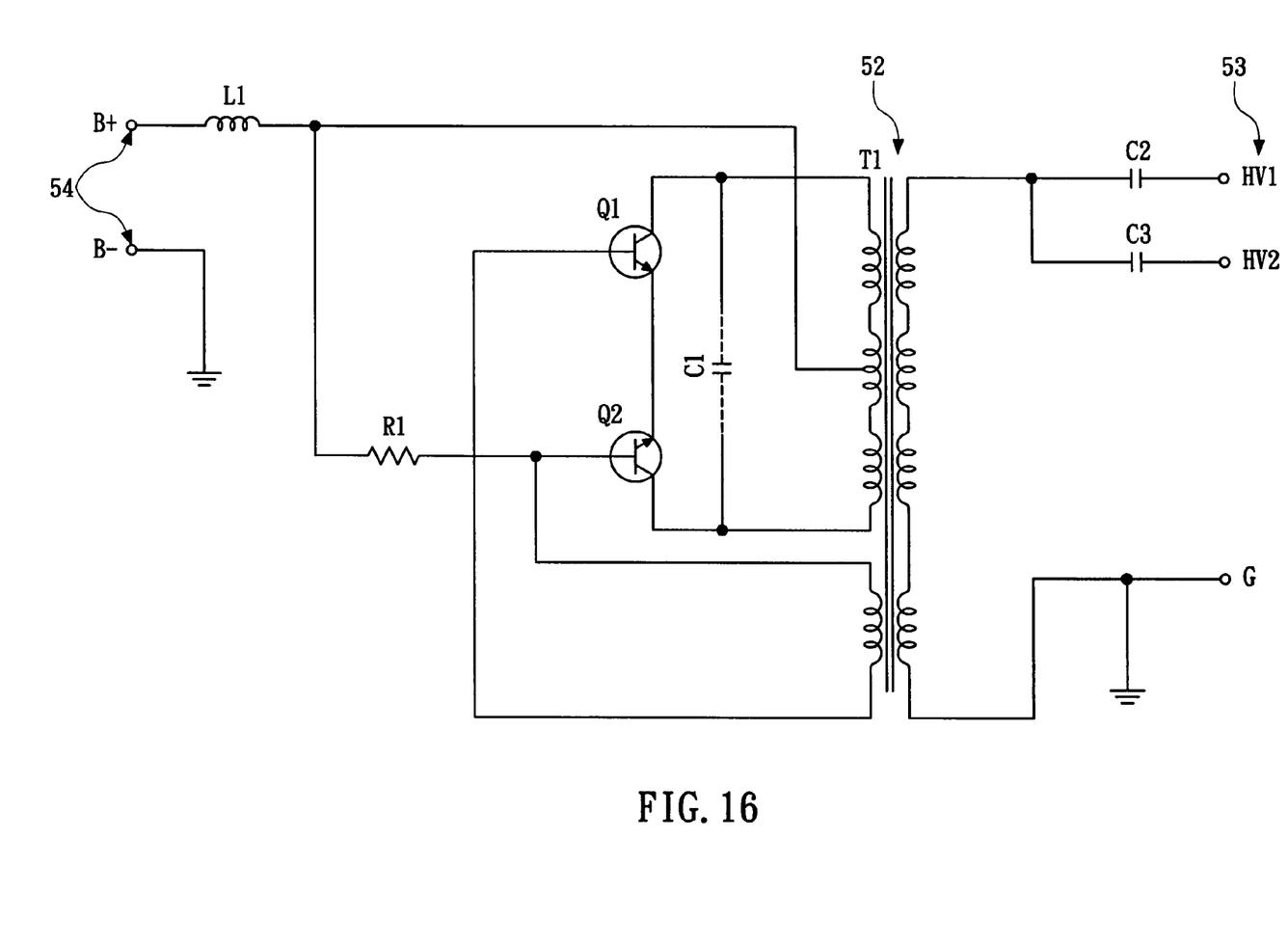
FIG. 16 is a circuit diagram of the ozone generator module of FIG. 14.

As shown in FIGS. 14, 15, and 16. Due to the fact that receivers 4 or recharger outlets can be larger than the average mouse, they are not restricted to the ozone generator module 2 described above, although the modulation and size of the ozone generator module 5 used is the superior design. In addition, the ozone generator module 5 uses the reestablished method of an ultraviolet light tube to produce ozone gas, however the structural design of the unit was changed to better meet modulation and size requirements. This includes a shell shaped insulator box 50 (such as the rectangular box 50 shown in FIGS. 14 and 15). There is a circuit board installed in the lower portion of the insulator box 50, and is installed with a small transformer 52 that can change the low voltage nature of mouses to high voltage, low current. In addition, an ultraviolet light tube 53 is connected to the outside of the circuit board, and 2 wires (negative and positive) are connected from the circuit board to the power supply. The interior of the insulation box 50 is lined with a layer of insulation resin (such as Epoxy) to contain and insulate the circuit board. This structure effective reduces size of the ozone generator module 5, thus allowing it to be easily installed in the receiver 4 or charge outlet. During use, the high voltage electricity in the ultraviolet light tube 53 causes the ultraviolet light tube 53 to continuously produce ozone gas. A small fan 44 can then be installed in the receiver 4, blowing the air towards the ultraviolet light tube 53, thus efficiently increasing the amount of ozone dispelled through the vent 42.

While preferred embodiments have been shown and described, various modifications and substitutions may be made without departing form the spirit and scope of the invention. Accordingly, it is to be understood that the present invention has been described by way of example, and not by limitation.

What is claimed is:

1. An ozone disinfecting non-cordless mouse comprising: an upper carapace; a lower carapace; internal parts including a microcontroller circuit board and optical coordinate device; output buttons; and a reel wheel;
said mouse being connected to a computer through a USB (Universal Serial Bus) plug; and
said mouse outfitted with an internal ozone generator module connected to power cord from said USB plug, such that said ozone generator module being operated utilizing a power supply from said computer connected to said mouse,
whereby said mouse can then dispel ozone gas through a suitable vent in said upper carapace, thus disinfecting the body of said mouse or a surrounding area of said mouse, and disinfect or clean the surrounding air.

2. The ozone disinfecting non-cordless mouse of claim 1, wherein said ozone generator module is installed in a shell shaped insulated box.

3. The ozone disinfecting non-cordless mouse of claim 2, wherein said ozone generator module includes a circuit board which is installed in the lower part of said insulated box for said ozone generator module.

4. The ozone disinfecting non-cordless mouse of claim 3, further comprising a transformer installed on said circuit board to allow said mouse to be changed from low voltage to high voltage, low current.

5. The ozone disinfecting non-cordless mouse of claim 4, an further comprising electrode board having holes, each lined up with each of plurality of opposing electrode pins of said ozone generator module.

6. The ozone disinfecting non-cordless mouse of claim 5, wherein said circuit board has two wires, one having negative polarity and another having a positive polarity, said wires connect said board to said USB plug power supply of said mouse.

7. The ozone disinfecting non-cordless mouse of claim 6, wherein the interior of said insulated box is covered with a layer of insulation resin to help cover said circuit board and provide insulation.

8. The ozone disinfecting non-cordless mouse of claim 1, further comprising a boundary line between the upper carapace and the lower carapace and a port on an exterior of said upper carapace.

* * * * *